United States Patent
Ratnayake et al.

(10) Patent No.: US 6,923,895 B2
(45) Date of Patent: Aug. 2, 2005

(54) COATED CAPILLARY ELECTROPHORESIS TUBES AND SYSTEM

(75) Inventors: Chitra K. Ratnayake, Yorba Linda, CA (US); Isabel C. Flores, La Mirada, CA (US)

(73) Assignee: Beckman Coulter, Inc., Fullerton, CA (US)

( * ) Notice: Subject to any disclaimer, the term of this patent is extended or adjusted under 35 U.S.C. 154(b) by 0 days.

(21) Appl. No.: 10/238,703

(22) Filed: Sep. 9, 2002

(65) Prior Publication Data

US 2004/0045828 A1 Mar. 11, 2004

(51) Int. Cl.$^7$ .......................... G01N 27/453; B05D 5/12
(52) U.S. Cl. ...................... 204/451; 204/454; 204/601; 427/299; 427/337
(58) Field of Search ................................ 204/601, 451, 204/454; 138/145, 146; 427/299, 337

(56) References Cited

U.S. PATENT DOCUMENTS

| | | | |
|---|---|---|---|
| 4,245,005 A | 1/1981 | Regnier et al. | 428/420 |
| 4,540,486 A | 9/1985 | Ramsden | 210/198.2 |
| 4,551,245 A | 11/1985 | Ramsden et al. | 210/198.2 |
| 4,640,909 A | 2/1987 | Ramsden et al. | 502/407 |
| 4,835,058 A | 5/1989 | Komiya et al. | 428/405 |
| 4,847,159 A | 7/1989 | Glajch et al. | 428/447 |
| 4,920,051 A | 4/1990 | Edmunds et al. | 435/215 |
| 4,929,560 A | 5/1990 | Edmunds et al. | 435/226 |
| 4,950,635 A | 8/1990 | Williams et al. | 502/401 |
| 4,985,577 A | 1/1991 | Shinohara et al. | 556/445 |
| 5,066,395 A | 11/1991 | Ramsden et al. | 210/198.2 |
| 5,085,779 A | 2/1992 | Crane et al. | 210/635 |
| 5,087,359 A | 2/1992 | Kakodkar et al. | 210/198.2 |
| 5,092,992 A | 3/1992 | Crane et al. | 210/198.2 |
| 5,137,627 A | 8/1992 | Feibush | 210/198.2 |
| 5,190,660 A | 3/1993 | Lindoy et al. | 210/670 |
| 5,209,976 A | 5/1993 | Ogawa | 428/391 |
| 5,326,895 A | 7/1994 | Kubota et al. | 556/445 |
| 5,356,433 A | 10/1994 | Rowland et al. | 623/11 |
| 5,599,625 A | 2/1997 | Wirth et al. | 428/391 |
| 5,653,875 A | 8/1997 | Betz et al. | 210/198.2 |
| 5,716,705 A | 2/1998 | Wirth et al. | 428/391 |
| 5,869,152 A | 2/1999 | Colon | 428/34.4 |
| 5,919,523 A | 7/1999 | Sundberg et al. | 427/333 |
| 5,955,377 A | 9/1999 | Maul et al. | 436/518 |
| 6,251,278 B1 | 6/2001 | Hammen | 210/635 |
| 6,258,454 B1 | 7/2001 | Lefkowitz et al. | 428/333 |
| 2002/0034580 A1 * | 3/2002 | Yang et al. | 427/2.11 |

OTHER PUBLICATIONS

Figeys et al, Journal of Chromatography B, 695 (1997) pp. 163–168.*
Smith et al, Electrophoresis 1993, 14, pp. 396–406.*
Towns, J.K.et al., *Polyethyleneimine–bonded phases in the separation of proteins by capillary electrophoresis*, Journal of Chromatography, (Sep. 7, 1990)516(1):69–78.

* cited by examiner

Primary Examiner—Kaj K. Olsen
(74) Attorney, Agent, or Firm—Sheldon & Mak; Jeffrey G. Sheldon; Kristin C. Hübner

(57) ABSTRACT

The invention is directed to a capillary tube for electrophoresis that has a positively charged coating on the capillary inner surface that prevents positively charged analytes from adsorbing to the inner capillary surface. The capillary tube has an inner surface that is coated with a first polymer layer having a plurality of polymer groups comprising polyethylene imine, designated herein as $(CH_2CH_2NH)_x$. The inner surface of the capillary typically has a second polymer layer covalently bonded to the first polymer layer. The invention includes a capillary tube where two or more than two polymer groups are covalently bonded to each other by a cross-linker. Also provided are an electrophoresis system the uses the coated capillary tubes, a method of performing electrophoresis that utilizes the coated capillary tubes, and a process for preparing the coated capillary tubes.

20 Claims, 2 Drawing Sheets

COATED CAPILLARY ELECTROPHORESIS TUBES AND SYSTEM

BACKGROUND

Figure 1:
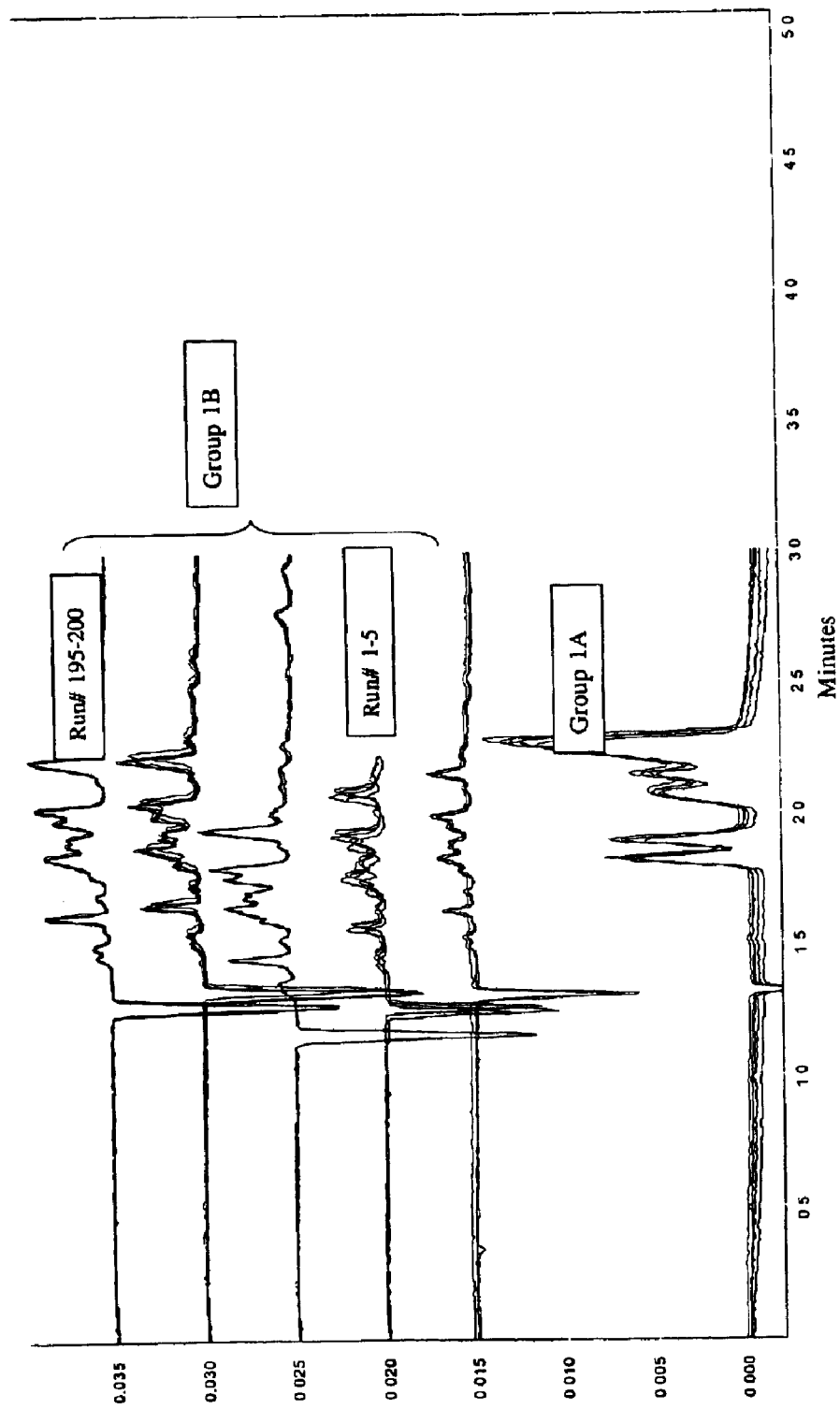

The following description provides a summary of information relevant to the present invention and is not an indication that any of the information provided or publications referenced herein is prior art to the presently claimed invention.

The electrokinetic separation of most analytes by electrophoresis is typically performed using buffers with wide range of pH (pH 3–10). Analytes such as peptides and proteins are positively charged under these buffer conditions. A popular and efficient way of performing electrokinetic separation on multiple samples is by capillary gel electrophoresis. Capillary gel electrophoresis systems typically employ fused silica capillary tubes. The surface of these fused silica capillary tubes is negatively charged above pH 2.0 because the silanol groups on the capillary surface become ionized. Consequently, the positively charged proteins and peptides traveling through the capillary during electrophoresis interact with the surface of the fused silica capillary and adsorb to the inner surface of the capillary tube. This is a problem because the adsorption of analytes continuously changes the surface properties of the capillary tube, resulting in changes in the electrosmotic flow velocity of the solution in the capillary. This causes a fluctuation of migration time of analytes which results in inaccuracies and poor reproducibility.

Attempts have been made to mitigate the adsorption of positively charged analytes to negatively charged fused silica capillaries. For example, capillary electrophoresis has been performed using running buffers with pH 2–4 to reduce the ionization of surface silanol groups. This approach can reduce the adsorption of analytes to a limited extent, but results in a reduction in sample throughput through the capillary and consequently longer run times. Also, attempts have been made to cover the capillary inner surface with neutral coatings. This approach also results in a reduction in sample throughput through the capillary. Capillary tubes having a positive coating have also been made, where monomeric amine silanes are covalently bonded to the capillary surface. A problem with these coatings is that they are unstable under acidic and basic conditions. None of the approaches used thus far have been ideal. What is needed are capillary tubes that are coated to obtain a longer run life, that can typically be used one hundred or more analysis with reproducible results, and that can be prepared by a fast and simple process. Also needed are capillary tubes and a capillary electrophoresis system that is useful for high-throughput analysis of proteins, peptides, and other analytes that adhere to capillary tubes during electrophoresis.

SUMMARY

The invention satisfies this need. The invention provides a capillary tube for electrophoresis that has a positively charged coating on the capillary inner surface that prevents positively charged analytes from adsorbing to the inner capillary surface. The capillary tube comprises an inner surface and an outer surface. At least a portion of the inner surface is coated with a first polymer layer having a plurality of polymer groups comprising $(CH_2CH_2NH)_x$ attached by a first linker group to an first anchor group. The first anchor group is covalently bonded to the inner surface of the capillary.

The inner surface of the capillary typically further comprises a second polymer layer covalently bonded to the first polymer layer. As compared to a single layer, this additional layer results in a higher density of positive charges on the wall surface that facilitates an increase in sample flow through the capillary. The second polymer layer has a plurality of polymer groups comprising $(CH_2CH_2NH)_x$ attached by a second linker group to a second anchor group that is covalently bonded to a first anchor group of a polymer group from the first polymer layer. In this formula, "x" represents an integer independently selected for individual polymer groups within the first polymer layer or second polymer layer. The first polymer layer covalently bonded to the inner surface of the capillary rube and the second polymer layer covalently bonded to the first polymer can be represented as illustrated below, where CS represents the inner surface of the capillary tube, N is nitrogen, O is oxygen, Si is silicon, x and y are integers between 7 and 15 independently selected for individual polymer groups, $R_1$ is selected from the group consisting of hydrogen, alkyl groups and halogens, $R_2$ and $R_3$ are independently selected from the group consisting of hydrogen, alkyl groups, and $(CH_2CH_2NH)_z$ where z is an integer between 1 and 15, n and m are integers between 1 and 8 that are independently selected for individual polymer groups, CR is a cross-linker that covalently bonds one or more $(CH_2CH_2NH)_x$ polymer group to one or more $(CH_2CH_2NH)_y$ polymer group, and H is hydrogen, with the proviso that H is not present when the N to which it is attached is cross-linked to a CR group.

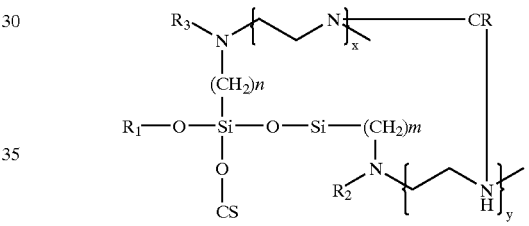

The invention includes a capillary tube for electrophoresis having an inner surface coated with a first polymer layer having the following structure:

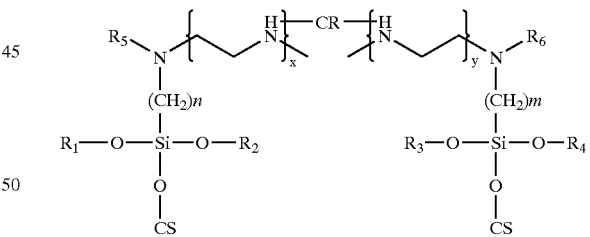

where CS is the inner surface of the capillary tube, N is nitrogen, O is oxygen, Si is silicon, $R_1$, $R_2$, $R_3$, and $R_4$ are independently selected from the group consisting of hydrogen, alkyl groups and halogens, $R_5$ and $R_6$ are independently selected from the group consisting of hydrogen, alkyl groups, and one or more than one $(CH_2CH_2NH)$ moiety, where y and y are integers between 7 and 15, n and m are integers independently selected for individual polymer groups that is between 1 and 8, CR is a cross-linker that covalently bonds one or more $(CH_2CH_2NH)_x$ polymer groups to one or more $(CH_2CH_2NH)_x$ polymer group to one or more $(CH_2CH_2NH)_y$ polymer group, and H is hydrogen, with the proviso that H is not present when the N to which it is attached is cross-linked to a CR group.

Also provided is a capillary electrophoresis system comprising a capillary tube coated according to the description herein, means for supporting the capillary tube, means for introducing a sample onto the capillary tube, means for performing electrophoresis on the sample, and means for detecting the sample. In one embodiment, the system incorporates a capillary tube having the following structure:

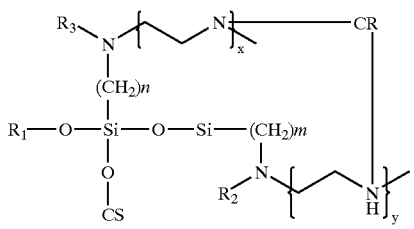

where CS is the inner surface of the capillary tube, N is nitrogen, O is oxygen, Si is silicon, x and y are integers independently selected for individual polymer groups that are between 7 and 15, $R_1$ is selected from the group consisting of hydrogen, alkyl groups and halogens, $R_2$ and $R_3$ are independently selected from the group consisting of hydrogen, alkyl groups, and $(CH_2CH_2NH)_z$ where z is an integer between 1 and 15, n and m are integers independently selected for individual polymer groups that are between 1 and 8, CR is a cross-linker that covalently bonds one or more $(CH_2CH_2NH)_x$ polymer group to one or more $(CH_2CH_2NH)_y$ polymer group, H is hydrogen, with the proviso that H is not present when the N to which it is attached is cross-linked to a CR group.

Further provided is a method of performing electrophoresis comprising the steps of providing a capillary electrophoresis apparatus, selecting a capillary tube according to the description herein, filing the capillary tube with a gel to form a capillary gel, providing a sample comprising one or more than one compound, loading the sample onto the capillary gel, performing electrophoresis on the sample, and detecting one or more than one compound from the sample.

Finally, the invention includes a process for the preparation of a silica capillary tube with a coating comprising the steps of treating the inner surface of the silica capillary tube with a base, treating the inner surface of the capillary tube with a solution containing between 2% and 30% trimethoxysilylpropyl (polyethyleneimine), rinsing the inner surface of the capillary tube, and treating the inner surface with a cross linker to cross link the polymer groups.

THE DRAWINGS

These features, aspects and advantages of the present invention will become better understood with regard to the following description, appended claims and accompanying figures where:

FIG. 1 illustrates an electrophoresis separation profile produced from samples run on coated capillary tubes according to the invention electrophoresed in a separation buffer of 5% acetonitrile in 95% 0.5N acetic acid at 400 v/cm field strength. Group 1A represents first five runs of five peptide standards. Group 1B represents 200 runs of horse heart cytochrome c digest.

Figure 2:
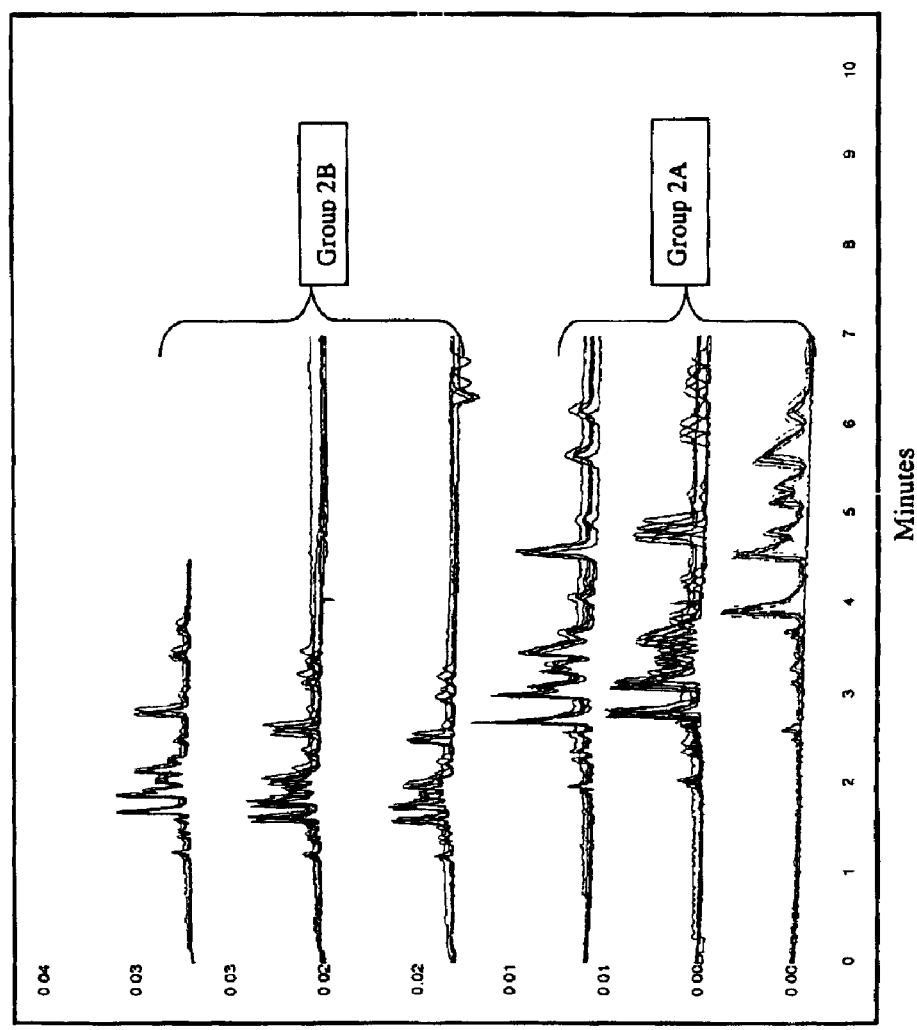

FIG. 2 illustrates an electrophoresis separation profile produced from samples run on uncoated prior art capillary tubes in a separation buffer of 5% acetonitrile in 95% 0.5N acetic acid. Group 2A represents horse heart cytochrome c run at 400 v/cm. Group 2B represents horse heart cytochrome c run at 666 v/cm.

DESCRIPTION

The following discussion describes embodiments of the invention and several variations of these embodiments. This discussion should not be construed, however, as limiting the invention to those particular embodiments. Practitioners skilled in the art will recognize numerous other embodiments as well. In all of the embodiments described herein that are referred to as being preferred or particularly preferred, these embodiments are not essential even though they may be preferred.

Chemical Structure of Polymer Groups

The invention is directed to coated capillary tubes for electrophoresis. The capillary tubes have an inner surface and an outer surface. The inner surface of a capillary tube is coated with a first polymer layer comprising a plurality of polymer groups. Each polymer group comprises x representing an integer that is typically between 1 and about 50 for each polymer group. More typically, x is between 7 and 15 for each polymer group. In preferred embodiments, substantially all of the polymer groups comprise linear chains of $(CH_2CH_2NH)_x$ covalently bonded to nitrogen. In other embodiments, the polymer groups comprise branched chains where one or more than one nitrogen is a secondary or tertiary amine covalently bound to one or more $(CH_2CH_2NH)_x$ groups.

One or more $(CH_2CH_2NH)_x$ moiety of a polymer group is attached by a first linker group to an first anchor group. Typically, the first and second linker group is an alkyl group having between 1 carbon atom and 6 carbon atoms. In one embodiment, the alkyl group has 3 carbon atoms and the alkyl group is a propyl group. Larger alkyl groups are possible, and chemical moieties other than alkyl groups can that covalently bond to $(CH_2CH_2NH)_x$ moieties can be used as linkers. The first anchor group is covalently bonded to the inner surface of the capillary. In the embodiment illustrated in structure I below, the anchor group comprises a silicon atom bonded to constituent groups $R_1$ and $R_2$ selected from the group consisting of hydrogen, alkyl groups, alkoxy groups, and halogens, and the linker group is an alkyl group with the number of carbons represented by the integer n.

(I)

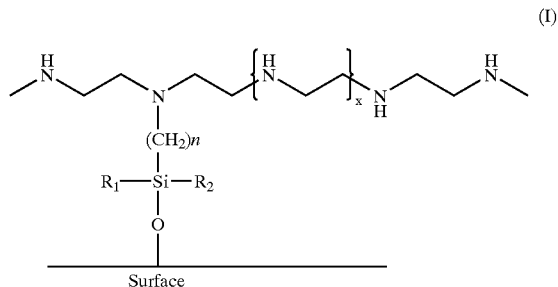

Typically the inner surface of the capillary tube comprises a silica, and the Si of anchor group is covalently bonded to the silica surface. Alternatively, the anchor group is another chemical moiety or a chemical moiety of the linker group that is covalently bound to the inner surface of the capillary. As illustrated in structure II below, embodiments where one polymer group is attached to a capillary surface through more than one anchor group are within the scope of the invention.

(II)

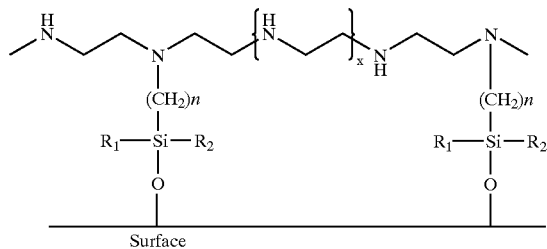

(IV)

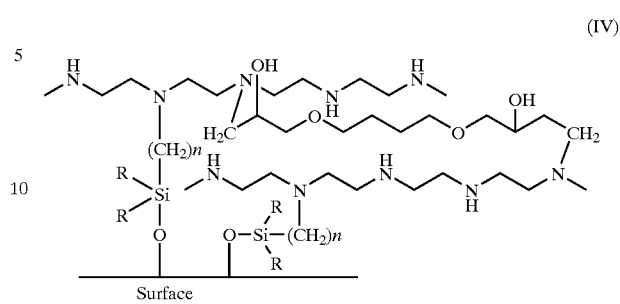

Cross-Linking of Polymer Groups

In another aspect of the invention, one or more $(CH_2CH_2NH)_x$ group from two or more than two different polymer groups are covalently bonded to each other by a cross-linker. The capillary tube has an inner surface and an outer surface, with the inner surface being coated with a first polymer layer. The first polymer layer comprises a plurality of polymer groups, each comprising $(CH_2CH_2NH)_x$, where x is an integer greater than 5. In alternative embodiments, x is an integer between 1 and 50, and more typically between 7 and 15. Two or more than two polymer groups are covalently bonded to each other by a cross-linker. Typically, the cross-linker is selected from the group consisting of 1,4-butanediol diglicidylether (BUDGE), ethylene glycol diglycidyl ether, triglycidyl glycerol, and diglycidyl glycerol. Each polymer group is attached by a linker group to an anchor group, and the anchor group is covalently bonded to the inner surface of the capillary.

In an exemplary embodiment, the inner surface of a capillary tube is coated with a first polymer layer having the following structure:

(III)

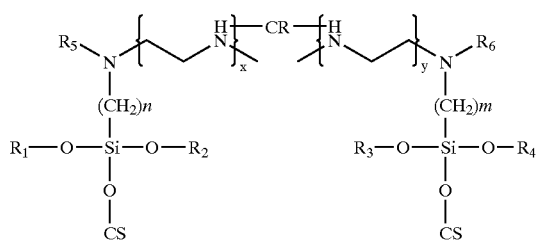

where CS represents the inner surface of the capillary tube, N is nitrogen, O is oxygen, Si is silicon, $R_1$, $R_2$, $R_3$, and $R_4$ are independently selected from the group consisting of hydrogen, aikyl groups and halogens, $R_5$ and $R_6$ are independently selected from the group consisting of hydrogen, alkyl groups, and one or more than one $(CH_2CH_2NH)$ moiety, where y and y are integers between 7 and 15, n and m are integers independently selected for individual polymer groups that is between 1 and 8, CR is a cross-linker that covalently bonds one or more $(CH_2CH_2NH)_x$ polymer group to one or more $(CH_2CH_2NH)_y$ polymer group, and H is hydrogen, with the proviso that H is not present when the N to which it is attached is cross-linked to a CR group. Preferably, $R_1$, $R_2$, $R_3$, and $R_4$ are halogens. Preferably $R_5$ and $R_6$ comprise $(CH_2CH_2NH)_x$, where x is an integer greater between 1 and 6.

In a preferred embodiment, the cross-linker is 1,4-butanediol diglicidylether and the coated capillary has structure (IV) illustrated below, where n is an integer between 1 and 7 and R represents constituent groups independently selected from hydrogen, alkyl groups, alkoxy groups and halogens.

Additional Polymer Layers

Variations of this capillary tube further comprise a second polymer layer covalently bound to the first polymer layer, and optionally additional polymer layers covalently bonded to successive layers. An exemplary structure having a first polymer layer and a second polymer layer is illustrated in structure V below, where each R constituent group is independently selected from the group consisting of hydrogen, alkyl groups, alkoxy groups and halogens, and n is an integer between 1 and 7.

(V)

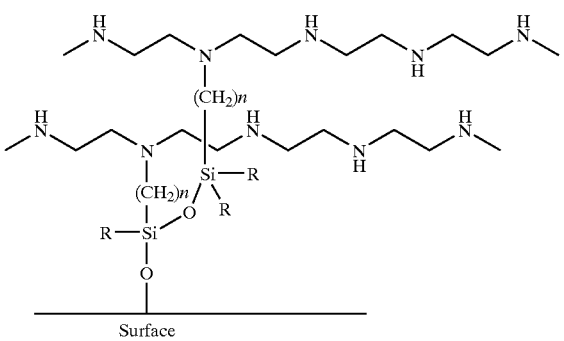

In one embodiment, one or more polymer group from the first polymer layer and one or more polymer groups from the second polymer layer are covalently bonded by a cross-linker. A capillary having a first and a second polymer layer can, as an example, have structure (VI) illustrated below.

(VI)

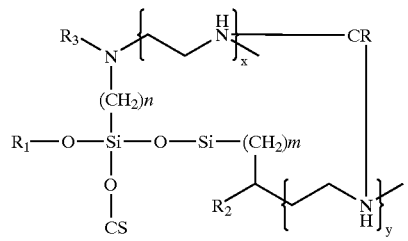

where CS is the inner surface of the capillary tube, N is nitrogen, O is oxygen, Si is silicon, x and y are integers between 7 and 15 independently selected for individual polymer groups, $R_1$ is selected from the group consisting of hydrogen, alky groups and halogens, $R_2$ and $R_3$ are independently selected from the group consisting of hydrogen, alkyl groups, and $(CH_2CH_2NH)_z$ where z is an integer between 1 and 15, n and m are integers between 1 and 8 that are independently selected for individual polymer groups, CR is a cross-linker that covalently bonds one or more $(CH_2CH_2NH)_x$ polymer group to one or more $(CH_2CH_2NH)_y$ polymer group, and H is hydrogen, with the proviso that H is not present when the N to which it is attached is cross-linked to a CR group. More typically, the integers n and m are between 3 and 5.

Alternatively, one or more polymer group from the same polymer layer are cross-linked by a cross-linker, or more than two polymer layers are present and cross-linked to other layers.

Electrophoresis System

The invention further includes a capillary electrophoresis system comprising a capillary tube as described herein, means for supporting the capillary tube, means for introducing a sample onto the capillary tube, means for performing electrophoresis on the sample, and means for detecting the sample. Exemplary capillary electrophoresis systems useful for performing electrophoresis include the P/ACE 2000 series, P/ACE 5000 series or P/ACE MDQ Capillary Electrophoresis Systems (Beckman Instruments, Inc., Fullerton, Calif.). Other capillary electrophoresis systems are described in "CEQ 2000 DNA Analysis System Performance", Nora M. Galvin et al., Technical Information #T-1854A, Beckman Coulter, Inc., 1998; U.S. Pat. No. 5,120,413, by Chen; Fu-Tai A. et al., entitled "Analysis of samples utilzing capillary electrophoresis"; U.S. Pat. No. 5,228,960, by Liu; Cheng-Ming et al., entitled "Analysis of samples by capillary electrophoretic immunosubtraction"; U.S. Pat. No. 5,891,313 by Johnson; Ben F., et al., entitled "Entrapment of nucleic acid sequencing template in sample mixtures by entangled polymer networks"; the contents of which are all hereby incorporated by reference in their entirety.

The capillary tube of the electrophoresis system can be represented by structure (VII) illustrated below.

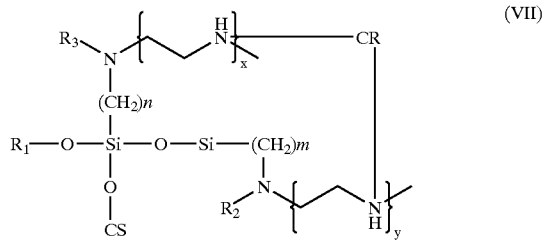

(VII)

In the above structure CS represents the inner surface of the capillary tube, N is nitrogen, O is oxygen, Si is silicon, x and y are integers independently selected for individual polymer groups that are between 7 and 15, $R_1$ is selected from the group consisting of alkyl groups and halogens, $R_2$ and $R_3$ are independently selected from the group consisting of hydrogen, alkyl groups, and $(CH_2CH_2NH)_z$ where z is an integer between 1 and 15, n and m are integers independently selected for individual polymer groups that are between 1 and 8, CR is a cross-linker that covalently bonds one or more $(CH_2CH_2NH)_x$ polymer group to one or more $)CH_2CH_2NH)_y$ polymer group, and H is hydrogen, with the proviso that H is not present when the N to which it is attached is cross-linked to a CR group.

Electrophoresis Methods

The invention further includes a method of performing electrophoresis. The method comprises the steps of providing a capillary electrophoresis apparatus, selecting a capillary tube describes herein, filing the capillary tube with a gel or separation buffer to form a capillary gel, providing a sample comprising one or more than one compound; loading the sample onto the capillary gel, performing electrophoresis on the sample, and detecting one or more than one compound from the sample. FIGS. 1 and 2 illustrate the enhanced elecrophoretic separation that is achieved by using the coated capillary tubes according to the invention. The conditions for performing electrophoresis are described in more detail in Example II below.

Process for Preparing Coated Capillary Tubes

The invention further includes a process for the preparation of a silica capillary tube with a coating. The process generally comprises the steps of sequentially treating the inner surface of the silica capillary tube with a base; acid, water and methanol; treating the inner surface of the capillary tube with a solution containing between 2% and 30% trimethoxysilylpropyl (polyethyleneimine); rinsing the inner surface of the capillary tube; and treating the inner surface with a cross linker to cross link the polymer groups. The detailed steps for preparing a coated capillary tube according to the invention are described below in Example I.

EXAMPLE I

Preparation of Silica Capillary Tubes with a Cross-Linked Coating

Trimethoxysilylpropyl (polyethyleneimine) (PEI silane) is a linear polyethyleneimine attached to trimethoxy silyl propyl groups. PEI silane was dissolved in methanol to obtain a 5% (v/v) solution of PEI silane in methanol by vortexing for 3 min in a glass vial. A capillary tube was first treated with methanol, then water, and then with 1.0 N Sodium Hydroxide and 1.0 N hydrochloric acid. The capillary was rinsed with deionized water, and afterward with methanol. The PEI silane solution was pumped through the capillary for 12–16 h at room temperature. After this, the capillary was rinsed briefly with methanol. Next, a 10% (v/v) solution of 1,4-Butanediol diglicidylether (BUDGE) in 1,4-Dioxane was pumped through the capillary for 4–6 h at room temperature to cross-link those polymer chains. After this, nitrogen was passed through the capillary while heating it for 1.0 h at 80° C. The capillary was then rinsed thoroughly with methanol. The cross-linking of the polymer chains on the capillary surface enhances the stability of the coating. The trimethoxysilylpropyl (polyethyleneimine) forms a covalent bond between the polymer and the silica capillary surface via trimethoxy silane groups attached to the polymer. Amine groups present in the polymer electrostatically bind to the surface by interacting with silanol groups on the surface. This creates a tightly bound layer of PEI silane on the surface. Crosslinking of these polymer molecules is achieved by reacting amine groups of the polymer with the epoxy groups in BUDGE. Capillary tubes coated by this process provides a stable coating with a enhanced coating coverage on the silica capillary surface, and in use the capillaries effectively suppress the adsorption of analytes and maintain a high electrosmotic flow.

EXAMPLE II

Comparison of Electrophoresis Run Profiles for Coated and Uncoated Capillary Tubes.

FIG. 1 illustrates separation profiles obtained from PEI silane and BUDGE coated fused silica capillary tubes. The capillary tubes had a 40 μm internal diameter, a 364 μm outer diameter, a 31 cm total length, and were coated according to example I. Electrophorsis was performed at 400 v/cm field strength on a Beckman Coulter P/ACE MDQ capillary electrophoresis system, available from Beckman Instruments, Inc. (Fullerton, Calif.). Group 1A of FIG. 1 shows the electropherograms obtained from the first five runs of five peptide standards. Group 1B in FIG. 1 shows electropherograms obtained up to 200 runs of Horse heart Cytochrome c. The electropherogram shows that migration time of analytes were stable from the first run and thereafter, and that the electrophoretic separation took only 2.3 min to complete. FIG. 2 illustrates separation profiles obtained from bare uncoated fused silica capillary tubes having a 40 μm internal diameter, a 364 μm outer diameter, and a 31 cm total length. In the experiments illustrated in FIGS. 1 and 2 the separation buffer used for electrophoresis was 5% acetonitrile in 95% 0.5N acetic acid. In FIG. 2, the bottom three groups of electropherograms were obtained at 400 v/cm field strength while the other upper three groups of electropherograms were obtained at 666 v/cm field strength. The bottom two groups show that the electrophoretic migration of peptides was not stabilized at the beginning of the run, as it was when the coated capillary tubes of the invention were used, and that it took about 7 min to complete the separation.

The experiments described in Example II demonstrate that the coated capillary tubes of the invention produced electrophoresis runs resulting in faster analyte separation and improved run-to-run reproducibility.

Having thus described the invention, it should be apparent that numerous modifications and adaptations may be resorted to without departing from the scope and fair meaning of the instant invention as set forth hereinabove and as described hereinbelow by the claims.

Although the present invention has been described in considerable detail with reference to certain preferred versions thereof, other versions are possible. Therefore, the spirit and scope of the appended claims should not be limited to the description of the preferred versions described herein.

All features disclosed in the specification, including the claims, abstracts, and drawings, and all the steps in any method or process disclosed, may be combined in any combination, except combinations where at least some of such features and/or steps are mutually exclusive. Each feature disclosed in the specification, including the claims, abstract, and drawings, can be replaced by alternative features serving the same, equivalent or similar purpose, unless expressly stated otherwise. Thus, unless expressly stated otherwise, each feature disclosed is one example only of a generic series of equivalent or similar features.

Any element in a claim that does not explicitly state "means" for performing a specified function or "step" for performing a specified function, should not be interpreted as a "means" or "step" clause as specified in 35 U.S.C. § 112.

What is claimed is:

1. A capillary tube for electrophoresis, the capillary tube having an inner surface and an outer surface, at least a portion of the inner surface coated with a first polymer layer, the first polymer layer comprising a plurality of polymer groups comprising $(CH_2CH_2NH)_x$ attached by a first linker group to a first anchor group, the first anchor group being covalently bonded to the inner surface of the capillary, the inner surface of the capillary further comprising a second polymer layer covalently bonded to the first polymer layer, the second polymer layer comprising a plurality of polymer groups comprising $(CH_2CH_2NH)_x$ attached by a second linker group to a second anchor group where x is an integer independently selected for individual polymer groups within the first or second layer, and the second anchor group being covalently bonded to a first anchor group of a polymer group from the first polymer layer.

2. The capillary tube of claim 1, wherein the first and second linker groups are an alkyl group having between 1 carbon atom and 6 carbon atoms.

3. The capillary tube of claim 2, wherein the alkyl group has 3 carbon atoms.

4. The capillary tube of claim 1, wherein x is between 7 and 15 for each polymer group.

5. The capillary tube of claim 1, wherein substantially all of the polymer groups comprise linear chains of $(CH_2CH_2NH)_x$.

6. The capillary tube of claim 1, wherein at least some individual polymer groups comprise branched chains where one or more than one nitrogen is a secondary or tertiary amine covalently bound to one or more $(CH_2CH_2NH)_x$ group.

7. The capillary tube of claim 1, wherein one or more $(CH_2CH_2NH)_x$ group from two or more than two different polymer groups are covalently bonded to each other by a cross-linker.

8. The capillary tube of claim 7, wherein the cross-linker is selected from the group consisting of: 1,4-butanediol diglicidylether, ethylene glycol diglycidyl ether, triglycidyl glycerol, and diglycidyl glycerol.

9. The capillary tube of claim 1, wherein the first polymer layer covalently bonded to the inner surface of the capillary tube and the second polymer layer covalently bonded to the first polymer layer has the following structure:

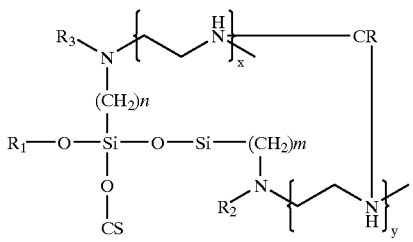

wherein CS is the inner surface of the capillary tube, N is nitrogen, O is oxygen, Si is silicon, x and y are integers between 7 and 15 independently selected for individual polymer groups, $R_1$ is selected from the group consisting of hydrogen, alkyl groups and halogens, $R_2$ and $R_3$ are independently selected from the group consisting of hydrogen, alkyl groups, and $(CH_2CH_2NH)_z$ where z is an integer between 1 and 15, n and m are integers between 1 and 8 that are independently selected for individual polymer groups, CR is a cross-linker that covalently bonds to one or more $(CH_2CH_2NH)_x$ polymer group to one or more $(CH_2CH_2NH)_y$ polymer group, and H is hydrogen, with the proviso that H is not present when the N to which it is attached is cross-linked to a CR group.

10. A capillary electrophoresis system comprising:

a capillary tube according to claim 1;

means for supporting the capillary tube;

means for introducing a sample onto the capillary tube;

means for performing electrophoresis on the sample; and means for detecting the sample.

11. The capillary electrophoresis system of claim 10, wherein the capillary tube has the following structure:

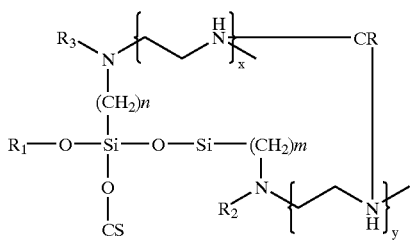

where CS is the inner surface of the capillary tube, N is nitrogen, O is oxygen, Si is silicon, x and y are integers independently selected for individual polymer groups that are between 7 and 15, $R_1$ is selected from the group consisting of alkyl groups and halogens, $R_2$ and $R_3$ are independently selected from the group consisting of hydrogen, alkyl groups, and $(CH_2CH_2NH)_z$ where z is an integer between 1 and 15, n and m are integers independently selected for individual polymer groups that are between 1 and 8, CR is a cross-linker that covalently bonds one or more $(CH_2CH_2NH)_x$ polymer group to one or more $(CH_2CH_2NH)_y$ polymer group, and H is hydrogen, with the proviso that H is not present when the N to which it is attached is cross-linked to a CR group.

12. A method of performing electrophoresis, the method comprising the steps of:
providing a capillary electrophoresis apparatus;
selecting a capillary tube according to claim 1;
filing the capillary tube with a gel to form a capillary gel;
providing a sample comprising one or more than one compound;
loading the sample onto the capillary gel;
performing electrophoresis on the sample; and
detecting one or more than one compound from the sample.

13. A capillary tube for electrophoresis, the capillary tube having an inner surface and an outer surface, at least a portion of the inner surface coated with a first polymer layer, the first polymer layer comprising a plurality of polymer groups, each polymer group comprising a polymer of the formula $(CH_2CH_2NH)_x$, which is attached by a linker group of the formula

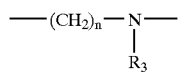

to an anchor group, the anchor group being covalently bonded to the inner surface of the capillary, where two or more than two polymer groups are covalently bonded to each other by a cross-linker, and where X is an integer greater than 5, $R_3$ is selected from the group consisting of hydrogen, alkyl groups, and $(CH_2CH_2NH)_z$ where z is an integer between 1 and 15, and n is an inteaer between 1 and 8.

14. The capillary tube of claim 13, wherein n is an integer between 1 and 6 carbon atoms.

15. The capillary tube of claim 14, wherein n is 3.

16. A capillary tube for electrophoresis, the capillary tube having an inner surface and an outer surface, at least a portion of the inner surface coated with a first polymer layer having the following structure:

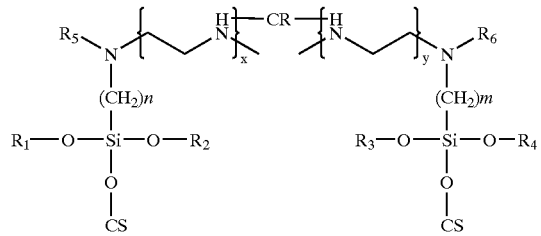

wherein CS is the inner surface of the capillary tube, N is nitrogen, O is oxygen, Si is silicon, $R_1$, $R_2$, $R_3$, and $R_4$ are independently selected from the group consisting of hydrogen, alkyl groups and halogens, $R_5$ and $R_6$ are independently selected from the group consisting of hydrogen, alkyl groups, and one or more than one $(CH_2CH_2NH)$ moiety, where x and y are integers between 7 and 15, n and m are integers independently selected for individual polymer groups that is between 1 and 8, CR is a cross-linker that covalently bonds one or more $(CH_2CH_2NH)_x$ polymer group to one or more $(CH_2CH_2NH)_y$ polymer group, and H is hydrogen, with the proviso that H is not present when the N to which it is attached is cross-linked to a CR group.

17. The capillary tube of claim 16, wherein the inner surface of the capillary tube further comprises a second polymer layer covalently bound to the first polymer layer.

18. The capillary tube of claim 17, wherein the inner surface of the capillary tube further comprises a third polymer layer covalently bonded to the second polymer layer.

19. The capillary tube of claim 16, wherein the cross-linker is selected from the group consisting of: 1,4-butanediol diglicidylether, ethylene glycol diglycidyl ether, triglycidyl glycerol, and diglycidyl glycerol.

20. A process for the preparation of the capillary tube of claim 16 comprising:
a) treating the inner surface of the capillary tube with a base;
b) treating the inner surface of the capillary tube with a solution containing between 2% and 30% trimethoxysilylpropyl (polyethyleneimine) to form a polymer group;
c) rinsing the inner surface of the capillary tube; and
d) treating the inner surface of the capillary tube with a cross-linker to cross-link at least one polymer group.

* * * * *